United States Patent [19]

Sears et al.

[11] 4,064,166

[45] Dec. 20, 1977

[54] ETHERIFICATION OF BARK EXTRACTS

[75] Inventors: Karl David Sears; Ronald Leroy Casebier, both of Shelton, Wash.

[73] Assignee: International Telephone and Telegraph Corporation, New York, N.Y.

[21] Appl. No.: 673,614

[22] Filed: Apr. 5, 1976

Related U.S. Application Data

[62] Division of Ser. No. 277,521, Aug. 3, 1972, Pat. No. 3,970,691.

[51] Int. Cl.$^2$ .................................... C07C 143/44
[52] U.S. Cl. ........................... 260/511; 260/465 F; 560/14
[58] Field of Search ............... 260/511, 512 R, 512 C, 260/465 F, 507 R, 433 C, 520, 345.2

[56] References Cited

U.S. PATENT DOCUMENTS

| | | | |
|---|---|---|---|
| 2,399,434 | 4/1946 | Graenacher et al. | 260/512 C |
| 2,831,022 | 4/1958 | Blaricom et al. | 260/512 R |
| 2,975,126 | 3/1961 | Blaricom et al. | 260/512 R |
| 2,999,108 | 9/1961 | Gray et al. | 260/512 R |
| 3,062,783 | 11/1962 | Gray et al. | 260/512 R |
| 3,335,167 | 8/1967 | Masson | 260/512 R |
| 3,658,829 | 4/1972 | Nakamura et al. | 260/473 G |
| 3,966,708 | 6/1976 | Casebier et al. | 260/345.2 |

Primary Examiner—Nicky Chan
Attorney, Agent, or Firm—J. B. Raden; H. J. Holt

[57] ABSTRACT

A derivative of coniferous tree barks is produced by reacting at elevated temperatures an alkaline polyphenolic solution of a coniferous bark extract in the proportion of from 0.1, and preferably from 0.5 to 8.0 moles of a carbonyl-activated halocompound per mole of monomeric unit in the polyphenol of the formula

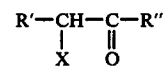

or with a cyano-activated halocompound of the formula

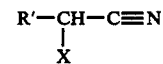

wherein R' is H, HC=O or R—C=O where R is alkyl or aryl; X is halogen and R" is alkyl, OH, oxyalkyl, aryl or OM in which M is a metal. The starting materials are the alkaline extracts resulting from the digestion of coniferous tree barks with an alkaline aqueous solution or preferably the sulfonated acid extracts of such barks. The reaction products are etherified polyphenolic compounds which are water-soluble and possess chelating characteristics.

4 Claims, No Drawings

ETHERIFICATION OF BARK EXTRACTS

This is a division of application Ser. No. 277,521 filed Aug. 3, 1972, now U.S. Pat. No. 3,970,691.

The present invention relates to etherified polyphenolic derivatives of coniferous barks and to a process for their preparation.

Bark from coniferous trees is a large volume by-product of the lumbering and pulping industries. Certain uses have been made of such bark by-product but the avilable supply still far exceeds the demand for presently available products derived from the bark. New uses and outlets for coniferous bark products and derivatives are therefore constantly being sought.

Etherification of phenols by reaction with carbonyl-activated or cyano-activated halocompounds in the presence of a base is known. Etherification of phenols in the presence of a base with chloroacetic acid to form aryloxyacetic acids is similarly known. However, insofar as is known, the preparation of such etherified compounds from bark polyphenolics has never previously been accomplished, nor is such an etherified product known.

It is an object of the present invention to provide a new class of useful compositions from bark, heretofore considered in large part a waste by-product of the lumbering and pulping industries.

It is an additional object of this invention to provide a water-soluble composition from such hitherto waste by-product which is useful in micronutrient formulations and as a chelating agent for waste-water purification.

It is still an additional object of this invention to provide a process for preparing etherified water-soluble derivatives of polyphenolic bark extracts by a relatively simple and economical process.

It has been discovered that the alkaline polyphenolic extract of coniferous tree barks may be converted into a water-soluble etherified polyphenolic derivative having a number of useful properties by reacting the extract with a caronyl-activated halocompound of the formula

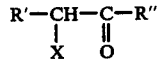

or with a cyano-activated halocompound of the formula

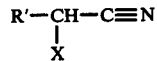

wherein R' is H, HC=O or R'—C=O in which R is alkyl or aryl; X is halogen and R" is alkyl, OH, oxyalkyl, or OM in which M is a metal such as sodium or potassium. It is believed that the process proceeds by a controlled nucleophilic substitution or displacement reaction in which an active hydroxyl hydrogen in the polyphenolic extract is alkylated with the cyano or carboxyl-activated halocompound. The starting materials are the alkaline extracts resulting from the digestion of coniferous barks with aqueous alkaline solutions or preferably the sulfonated acid salts of such extracts. The reaction products are etherified polyphenolic compounds which are water-soluble and possess chelating characteristics having utility in micronutrient formulations.

The bark extract used as a starting material in the process of the present invention may be the alkaline extract obtained by digesting coniferous barks as disclosed in U.S. Pat. Nos. 2,782,241, 2,819,295, or 2,823,223 all assigned to the present assignee. However, to obtain a more water-soluble reaction product, it is preferred that the starting material be a sulfonated extract of the type shown in U.S. Pat. No. 2,831,022, assigned to the present assignee. The latter patent discloses the digestion of coniferous barks at elevated temperatures in the presence of suitable amounts of an aqueous solution of a salt of sulfurous acid until most of the sulfurous acid salt radical is consumed and then drying the sulfonated bark extract.

The present reaction products are prepared by dissolving the foregoing bark extracts in an aqueous alkaline solution. The amount of base used depends on the amount of halocompound added. For example, reactions with chloroacetylacetone or monochloroacetone normally require an equivalent amount of base. Halocompound acids, such as chloroaceticacid, will require more than an equivalent because the acid must first be neutralized. From about 0.1 or preferably 0.5 to about 8 moles of the carbonyl or cyano-activated halocompound is utilized per mole of monomeric unit in the polyphenolic extract. The reaction is carried out at a temperature of from 50°–120° C for a period which will normally range from ½ to 8 hours. The reaction product is then separated from the excess reagents and recovered from the solution. The etherified products are obtained in yields ranging from about 78–188% by weight based on the weight of the polyphenolic bark extract used as a starting material.

Examples of suitable carbonyl-activated halo-compounds are halogen substituted monocarboxylic acids in which R' is an alkyl group and R" is OH in the formula

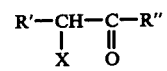

such as chloroacetic acid, chlorobutyric acid, the salts of such acids and the like. Ketones in which R is an alkyl group such as monochloroacetone of 3-chloroacetylacetone are illustrative of useful halogen substituted ketones. Esters in which R' is acetyl group and R" is an ethoxy group are also useful, such as 2-chloroethylacetoacetate. Useful salts (in which R" is OM) are the sodium and potassium salts of chloroacetic or chlorobutyric acid. Suitable cyanoactivated compounds are chloroacetonitrile and chloropropionitrile.

The reaction products of the invention possess utility in a number of applications. Their ferrous salts have demonstrated usefulness as micronutrient carriers in the treatment of chlorosis in soy beans. The presence of a number of functional groups in the reaction products indicates their utility as chelating agents for waste-water purification when in the form of salts, amides or cationic esters.

The following examples are illustrative of the practice of the invention. All parts are by weight unless otherwise indicated.

EXAMPLE 1

This example illustrates the reaction between a sulfonated bark extract and chloroacetic acid. The bark extract was prepared by digesting coniferous tree barks in an aqueous sulfurous acid solution having a pH of 5.83. The liquor was then concentrated and spray dried. This sulfonated extract (30 grams) in 25% sodium hydroxide solution (32 ml.) was placed in a round bottom flask (200 ml.) containing chloroacetic acid (9.8 g.) dissolved in water (20 ml.). The reaction mixture was placed in a boiling water bath for one hour and then cooled. The resulting cooled solution was diluted with water (750 ml.). The pH was adjusted to 3.5 with conc. hydrochloric acid (13.6 ml.), electrodialyzed and freeze dried. The yield was 30.6 grams of reaction product.

A number of samples were prepared by a procedure analogous to that described above. The amount of sulfonated extract employed was always 30 g. In the majority of samples prepared, a precipitate formed upon acidification of the solution to pH 3.5 prior to dialyses; the amount of the precipitate ranged from very small to sizeable. To two instances where the amount of precipitate was quite substantial, a separation was made by centrifuging. The decanted clear liquid was dialyzed and processed normally; the precipitate was suspended in water and freeze dried. During titration of these precipitated fractions, resolubilization occurred as the amount of added base increased. The precipitate dissolved completely before the titration end point was reached.

The results are set forth in the following Table I:

TABLE I

Reactions of Sulfonated Bark Extract with Chloroacetic Acid

| Sample No. | NaOH Conc. g/l. | NaOH equiv./ equiv. of Extract[1] | Equiv. of ClCH$_2$CO$_2$H /equiv. of Extract[1] | Time, Hr. | Yield of A fraction[2], Wt. % | Yield of B fraction[3], Wt. % | Product CO$_2$H; % for A, B | Product Net CO$_2$H, % for A, B |
|---|---|---|---|---|---|---|---|---|
| 1 Extract (unreacted) | | | | | | | 5.78 | |
| 2 | 183 | 1.03 | 0.53 | 1 | 78 | | 6.47 | 0.69 |
| 3 | 183 | 3.08 | 2.10 | 1 | 83 | | 10.78 | 5.00 |
| 4 | 183 | 6.16 | 4.18 | 1 | 81 | | 17.10 | 11.32 |
| 5 | 183 | 6.16 | 4.18 | 2 | 115 | | 20.28 | 14.50 |
| 6 | 183 | 12.32 | 8.00 | 1 | 66 | 55 | 27.53 | 21.75 |
| | | | | | | | 11.39 | 5.61 |
| 7 | 382 | 3.44 | 1.04 | 1 | 102 | | 15.46 | 9.68 |
| 8 | 382 | 6.88 | 2.34 | 1 | 168 | | 13.77 | 6.99 |
| 9 | 382 | 13.76 | 4.67 | 1 | 144 | 44 | 21.65 | 15.37 |
| | | | | | | | 9.93 | 4.15 |
| 10 | 382 | 5.15 | 2.34 | 2 | 105 | | 22.38 | 16.60 |
| 11 | 382 | 8.58 | 4.67 | 2 | 120 | | 24.97 | 19.19 |

[1]Molecular Wt. of 337/monomeric unit assumed for extract.
[2]Water-soluble material after acidification to pH 3.5.
[3]Water-insoluble material after acidification to pH 3.5.

EXAMPLE 2

This example illustrates the reaction of an alkaline coniferous bark extract with chloroacetic acid. The extract was prepared by digestion of a tree bark in an alkaline solution and then drying the liquor. This extract, the sodium salt of chloroacetic acid and sodium hydroxide (in 20 ml. water) were placed in a 250 ml. flask and the contents well mixed. The flask was sealed with a flexible rubber cap, inserted into an oil bath maintained at the temperature for the time period indicated and stirred magnetically. Upon cooling, 80 ml. of ethanol was added to the flask and the contents were well mixed. The product was filtered, washed with 20 ml. of an ethanol-water (80/20 by volume) mixture, then mixed in a beaker with 80 ml. of the same solvent, filtered again and finally washed on the filter with 50 ml. of the solvent. In experiments where an excess of sodium hydroxide (2.2 g. of additional NaOH per 10 g. of extract) were used, the product, a viscose oil, was washed by decanting rather than by filtering. The final product was dried at an elevated temperature to give 80 – 90% yield of solids.

A number of further samples were prepared following the above procedure, varying the reactant amounts and conditions. The results are set forth in Table II, following.

TABLE II

Reaction of Alkaline Extract with Choroacetic Acid

| Sample No. | Extract[1] grams | CH$_2$ClCOONa grams | Additional NaOH grams | Reaction Temp. °C | Reaction Time hours | Yield (grams) O.D. basis | Carboxylic Acid Content % COOH |
|---|---|---|---|---|---|---|---|
| 1 | 10 | 8.3 | 1.1 | 60 | 4 | 9.2 | 24.4 |
| 2 | 10 | 8.3 | 1.1 | 60 | 2 | 9.4 | 21.6 |
| 3 | 10 | 8.3 | 1.1 | 50 | 4 | 8.5 | 22.0 |
| 4 | 10 | 8.3 | — | 60 | 4 | 5.9 | 19.3 |
| 5 | 10 | 4.0 | 1.1 | 60 | 4 | 8.9 | 21.6 |
| 6 | 10 | 4.0 | 2.2 | 60 | 5 | 11.8 | 24.0 |
| 7 | 10 | 4.0 | — | 60 | 4 | 5.0 | 22.3 |
| 8 | 50 | 20.0 | 5.5 | 60 | 4 | 42.0 | 25.7 |
| 9 | 50 | 20.0 | 11.0 | 60 | 4 | 50.7 | 25.2 |
| 10 | 10 | 0 | 1.1 | 60 | 4 | 9.01 | 17.2 |

[1]Analysis: 10.1% moisture, 9.88 Na (by Flamephotometry).

EXAMPLE 3

This example illustrates the reaction of a sulfonated bark extract with monochloroacetone. The extract was the same as that used in Example 1. This extract (30 grams), sodium hydroxide solution (64 ml. containing 8 g. of NaOH) and an aqueous solution of monochloroacetone (40 ml. containing 19.6 g. of ClCH$_2$COCH$_3$) were placed in a round-bottom flask (500 ml.) equipped with a condenser. The reaction mixture was placed in a boiling water bath and stirred for 2 hours at 100° C.; the resulting cooled solution had a pH of 6.5. It was adjusted to pH 3.5 with concentrated hydrochloric acid (3.5 ml.), electrodialyzed and freeze dried, 54.6 g.

The following Table III sets forth the results of a number of samples prepared as set forth above.

for 2 hours; the resulting cooled solution (pH 5.0) was adjusted to pH 3.5 with conc. hydrochloric acid (3.5 ml.), electrodialyzed, and freeze dried to give 30.6 g. of reaction product.

A number of samples were prepared following the above procedure. The results are set forth in the following Table IV.

TABLE IV

| | | Reactions of Sulfonated Extract with 3-Chloroacetylacetone | | | | | | | |
|---|---|---|---|---|---|---|---|---|---|
| | | NaOH | | ClCHAc$_2$ | | | | | |
| Sample No. | Temp. °C. | g. | Equiv./mole of extract[1] | g. | Equiv./mole of extract[1] | Yield g. | wt., % | Reaction pH | Product C—CH$_3$ % |
| 1 | 100 | 4 | 1.12 | 13.4 | 1.12 | 34.0 | 113 | 4.5 | |
| 2 | 100 | 8 | 2.24 | 26.8 | 2.24 | 42.5 | 141 | 4.4 | |
| 3 | 60 | 4 | 1.12 | 13.4 | 1.12 | 29.0 | 97 | 5.6 | |
| 4 | 100 | 5 | 1.40 | 13.4 | 1.12 | 30.6 | 102 | 5.0 | 2.89 |
| 5 | 100 | 10 | 2.80 | 26.8 | 2.24 | 33.5 | 112 | 4.7 | 4.01 |
| 6 | 100 | 15 | 4.20 | 40.2 | 3.36 | 24.6 | 82 | 4.8 | 5.90 |
| 7 | 100 | 20 | 5.60 | 53.6 | 4.48 | 28.2 | 94 | 4.8 | |
| 8 | 60 | 10 | 2.80 | 26.8 | 2.24 | 29.8 | 99 | 6.1 | 2.01 |
| 9 | 60 | 20 | 5.60 | 4.48 | 4.48 | 42.2 | 141 | 6.1 | |

[1]MW of 337/monomeric unit assumed for extract

TABLE III

| | | Reactions of Sulfonated Bark Extract with Monochloroacetone | | | |
|---|---|---|---|---|---|
| Sample No. | Yield Wt. % | NaOH equiv./mole of extract[1] | Equiv. of ClCH$_2$C—CH$_3$/ mole of extract[1] | Final Reaction pH | Product C—CH$_3$ % |
| 1 | 91 | 1.12 | 1.12 | 6.49 | 1.76 |
| 2 | 77 | 2.24 | 2.24 | 6.38 | 4.77 |

[1]Molecular weight of 337/monomeric unit, assumed for extract.

1-Molecular weight of 337/monomeric unit, assumed for extract.

EXAMPLE 4

This example illustrates the preparation of a reaction product of a sulfonated bark extract and 3-chloroacetylacetone. The sulfonated extract was prepared as in Example 1. The chloroacetylacetone was prepared as follows.

Acetylacetone (2, 4-pentanedione, 210 g., 2.1 mole) was placed in a three-necked flask provided with a magnetic stirring bar, dropping funnel, condenser, thermometer and icebath. Sulfuryl chloride (286 g., 2.1 mole) was added dropwise, with stirring, over a period of 5 hours with a temperature of 0°-5° C. being maintained. The solution was then heated with stirring to 90°-95° C. for 0.25 hour to complete the reaction, cooled to 25° C. and extracted with 125 ml. of 10% aq. sodium bicarbonate solution. The organic solution was water-washed until neutral and then distilled at 54° C. (20 min.) to give the product. Redistillation of this material yielded 184.3 grams of 3-chloroacetylacetone.

Sulfonated bark extract (30 g.), sodium hydroxide solution (32 ml. H$_2$O containing 5 g. of NaOH) and an aqueous solution (20 ml.) of 3-chloroacetylacetone (13.4 g.) were placed in a round-bottom flask (250 ml.) equipped with a condenser. The reaction mixture was placed in a boiling water bath and magnetically stirred

EXAMPLE 5

This example illustrates the reaction of 2-chloroethylacetoacetate with the same sulfonated bark extract used in Example 4.

Sulfonated bark extract (30 g.), sodium hydroxide solution (64 ml. H$_2$O containing 10.0 g. NaOH) and an aqueous solution (40 ml.) of 2-chloroethylacetoacetate (33 g.) were placed in a round-bottom flask (500 ml.) equipped with a condenser. The reaction mixture was placed in a boiling water bath and stirred magnetically for two hours; the resulting cooled solution (pH 5.1) was adjusted to pH 3.5 with conc. hydrochloric acid (5.1 ml.). Some insoluble material which had formed at this point was discarded. The solution was electrodialyzed and freeze dried to produce 30.41 g. of reaction product.

The following Table V sets forth the results of the preparation of a number of samples in accordance with the procedure of Example 5.

TABLE V

| | | Reactions of Extract[1] with 2-Chloroethylacetoacetate | | | | | | | | |
|---|---|---|---|---|---|---|---|---|---|---|
| | | NaOH | | ClCH-COCH$_3$ CO$_2$C$_2$H$_5$ | | | | | Net | |
| Sample No. | Temp., °C. | g. | Equiv./mole of extract[1] | g. | Equiv./mole of extract[1] | Yield g. | Wt.,% | CO$_2$H % | CO$_2$H % | Final Rxn. pH |
| 1 Extract (reacted) | | | | | | | | 5.78 | | |
| 2 | 100 | 4 | 1.12 | 16.5 | 1.12 | 40.9 | 136 | | | 5.0 |
| 3 | 100 | 10 | 2.80 | 33.0 | 2.24 | 30.4 | 101 | 7.68 | 1.9 | 5.1 |
| 4 | 100 | 15 | 4.20 | 49.5 | 3.36 | 44.2 | 147 | 5.47 | | 5.1 |
| 5 | 60 | 10 | 2.80 | 33.0 | 2.24 | 33.2 | 110 | 7.53 | 1.75 | 7.0 |

[1]Molecular weight of 337/monomeric unit, assumed for extract.

EXAMPLE 6

This example illustrates the reaction of the sulfonated bark extract used in Example 5 with chloroacetonitrile.

The sulfonated bark extract (30 g.), sodium hydroxide solution (32 ml. containing 4.0 g. of NaOH) and an aqueous solution of chloroacetonitrile (20 ml. containing 8.0 g. of ClCH$_2$CN) were placed in a flask (250 ml.) equipped with a condenser. The reaction mixture was placed in a boiling water bath and stirred magnetically for two hours. The resulting cooled solution (pH-6.49) was freeze dried to produce 37.2 g. of reaction product.

The following Table VI sets forth the results of the preparation of a number of samples in accordance with this example.

TABLE VI

Reactions of Sulfonated Extract with Chloroacetonitrile

| Sample | NaOH g. | NaOH equiv./mole of extract[1] | ClCH$_2$CN g. | ClCH$_2$CN equiv./mole of extract[1] | Final Rxn. pH | Yield g. | Yield wt. % | Total N, % | CH$_2$CN Incorporation[3] % |
|---|---|---|---|---|---|---|---|---|---|
| 1 | 4 | 1.12 | 8 | 1.19 | 6.6 | 37.2 | 124 | 3.6[4] | 87 |
| 2[2] | 8 | 2.24 | 16 | 2.38 | 5.3 | 43.6 | 145 | 4.6 | 62 |
| 3[2] | 12 | 3.36 | 24 | 3.57 | 5.1 | 59.4 | 197 | 5.5 | 52 |

[1]Molecular weight of 337/monomeric unit, assumed for extract.
[2]Dialyzed, then reneutralized.
[3]Based on total N, %.
[4]After dialysis, % total N = 3.6.

Chelating agents useful in micronutrient formulations and other applications may be prepared from the ether of any of the foregoing examples by reaction with the desired metal salt, as for example, iron or zinc sulfate.

We claim:

1. Water soluble etherified polyphenolic derivatives of coniferous tree barks produced by reacting a sulfonated polyphenolic extract of a coniferous tree bark in the proportion of about 0.1 to 0.8 moles per mole of monomeric unit in the polyphenol with a halocompound selected from the group consisting of monochloroacetone and 3-chloroacetylacetone, said bark extract being sulfonated with a salt selected from the group consisting of ammonium, sodium and potassium salts of sulfurous acid, said reaction being carried out at a temperature of from about 50°–120° C. in an alkaline solution.

2. The etherified polyphenolic derivative of claim 1 in which the halocompound is monochloroacetone.

3. The etherified polyphenolic derivative of claim 1, in which the bark extract is reacted with from 0.5 to 8.0 moles of the halocompound per mole of monomeric unit in the polyphenol extract.

4. The etherified polyphenolic derivative of claim 1, in which the halocompound is 3-chloroacetylacetone.